United States Patent
Gross et al.

(10) Patent No.: US 8,323,356 B2
(45) Date of Patent: Dec. 4, 2012

(54) SULFONIMINES AS BLEACHING ACTIVATORS

(75) Inventors: Wibke Gross, Hueckelhoven (DE); Ralph Nemitz, Juechen (DE); Astrid Kroos, Monheim (DE); Katja Guenther, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/480,512

(22) Filed: May 25, 2012

(65) Prior Publication Data

US 2012/0227756 A1    Sep. 13, 2012

Related U.S. Application Data

(63) Continuation of application No. PCT/EP2010/063669, filed on Sep. 17, 2010.

(30) Foreign Application Priority Data

Nov. 27, 2009 (DE) .......................... 10 2009 047 250

(51) Int. Cl.
*D06L 3/00* (2006.01)
(52) U.S. Cl. ..................................... 8/101; 8/110; 8/111
(58) Field of Classification Search .............. 8/101, 110, 8/111

See application file for complete search history.

(56) References Cited

U.S. PATENT DOCUMENTS 5,047,163 A * 9/1991 Batal et al. .................... 510/116

OTHER PUBLICATIONS

STIC Search Report dated Jul. 16, 2012.*

* cited by examiner

*Primary Examiner* — Eisa Elhilo
(74) *Attorney, Agent, or Firm* — David LeCroy

(57) ABSTRACT

Agent for lightening keratinic fibers, particularly human hair, wherein the agent contains, in a cosmetic carrier, at least one oxidizing agent chosen from hydrogen peroxide and/or a solid addition product thereof with organic or inorganic compounds, and at least one sulfonimine of formula (I)—

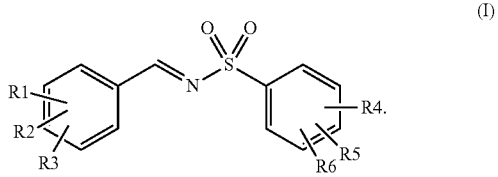

13 Claims, No Drawings

SULFONIMINES AS BLEACHING ACTIVATORS

CROSS REFERENCE TO RELATED APPLICATIONS

The present application is a continuation of International Application No. PCT/EP2010/063669 filed 17 Sep. 2010, which claims priority to German Patent Application No. 10 2009 047 250.9, filed 27 Nov. 2009, both of which are incorporated herein by reference.

BACKGROUND OF THE INVENTION

The present invention relates to agents for lightening keratinic fibers, particularly human hair, wherein the agents contain, in addition to a chemical oxidizing agent, at least one specific sulfonimine. Use of such an agent on keratinic fibers significantly improves the lightening performance of lightening and hair-bleaching agents. The present invention further relates to a multi-component packaging unit (kit of parts) for lightening keratinic fibers that comprises, packaged separately from one another, at least one agent containing a specific sulfonimine, an oxidizing agent preparation, and optionally a hair-bleaching powder.

Lightening of one's hair color has long been a desire of many consumers, since a blond hair color is regarded as attractive and as desirable in terms of fashion. A variety of hair-bleaching agents having different levels of hair-bleaching performance are commercially available for this purpose. The oxidizing agents present in these products are capable of lightening hair fibers by oxidizative destruction of the hair's own melanin dye. For a moderate hair-bleaching effect, it is sufficient to use hydrogen peroxide (optionally with the addition of ammonia or other alkalizing agents) as the only oxidizing agent. In order to achieve a more pronounced hair-bleaching effect, a mixture of hydrogen peroxide and peroxodisulfate salts and/or peroxomonosulfate salts is typically used.

Lightening is, unfortunately, also accompanied by damage to the hair, since not only the hair's dyes but also other structural constituents of the hair are damaged by oxidation. The extent of damage can range from hair that is coarse, brittle, and more difficult to comb out, to decreased hair strength and tear resistance, to actual hair breakage. The greater the amount of hydrogen peroxide and optional peroxodisulfate used, the greater the damage generally caused to the keratin fibers. Hair coloring or lightening agents having good lightening performance without at the same time damaging the hair fibers are not known to date.

The present invention report therefore provides novel agents for lightening or bleaching of hair that are comparable or superior in terms of their lightening performance to those agents typically available on the market, while at the same time having decreased hair damage. For consumers with very dark hair, it is not possible to generate light-colored blond shades even when using high concentrations of hydrogen peroxide in combination with persulfate salts. Repeated applications are also not possible because of increasing hair damage. The present invention therefore also makes available an agent whose lightening capability exceeds that of the currently marketed agents made up of hydrogen peroxide and peroxodisulfate salts (sodium peroxodisulfate, ammonium peroxodisulfate, and/or potassium peroxodisulfate).

A large number of organic compounds are mentioned in the literature as effective agents for activation of peroxo compounds. U.S. Pat. No. 5,047,163 and U.S. Pat. No. 5,041,232 disclose specific sulfonimines that, in the presence of peroxo compounds, particularly inorganic peroxo compounds such as peroxomonosulfates, and further adjuvants, produce improvements in bleaching behavior in textile bleaching. Use of the corresponding sulfonimines in hair-bleaching agents for the lightening of hair is not hitherto known. Use of the sulfonimine derivatives according to the present invention for the activation of peroxo compounds is therefore known from the literature. It is not known from the existing art, however, that the lightening effect on hair can also be intensified by the use of sulfonimines in cosmetic hair-bleaching agents.

Different application parameters, which in some cases differ sharply from one another, are chosen for textiles bleaching and hair lightening, so that experimental results from one application sector are not transferable to the other. For example, both the formulation and temperatures selected for the two bleaching processes are very different. It was therefore not foreseeable that the activation, demonstrated in the washing-agent sector, of peroxo compounds by the sulfonimine derivatives according to the present invention might result in an intensifying of the hair-bleaching effect in the bleaching of hair as well.

SUMMARY OF THE INVENTION

It has now been discovered, in unforeseeable fashion, that the use of a combination of sulfonimine derivatives according to general formula 1 and hydrogen peroxide lightens hair much more greatly than would have been possible by using a comparable amount of hydrogen peroxide alone.

As a result of the improved hair-bleaching performance when the agent according to the present invention is utilized, the amount of oxidizing agent used can be decreased and hair damage thereby minimized. A shortening of the contact time for achieving a lightening effect corresponding to the existing art is also thereby possible. In addition, these agents possess enhanced lightening performance compared to commercial lightening agents, and therefore allow even very dark hair to be lightened to light-colored blond shades.

Agents according to the present invention decolorize the natural melanin dye by oxidation. Synthetic dyes previously present on or in the keratin-containing fibers are also destroyed with the aid of the agents according to the present invention, and the fibers are thus bleached.

A first subject of the invention is therefore an agent for lightening keratinic fibers containing, in a cosmetic carrier
(i) at least one oxidizing agent selected from hydrogen peroxide and/or a solid addition product thereof with organic or inorganic compounds, and
(ii) at least one sulfonimine of formula (I)

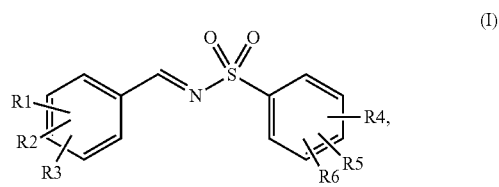

wherein
R1 to R6 are, mutually independently, a hydrogen atom, a halogen atom, a $C_1$ to $C_6$ alkyl group, a partly or entirely halogenated $C_1$ to $C_6$ alkyl group, a $C_2$ to $C_6$ alkenyl group, a $C_1$ to $C_6$ hydroxyalkyl group, a $C_2$ to $C_6$ polyhydroxyalkyl group, a $C_1$ to $C_6$ alkoxy group, a $C_1$ to $C_6$ alkoxy-$C_2$ to $C_6$ alkyl group, an aryl-$C_1$ to $C_6$ alkyl group, a hydroxy group, a nitrile group, a nitro group, a carboxylic acid group, a sulfonic acid group, a sulfonamido group, an amino group, a di-$C_1$ to $C_6$ alkylamino group, a mono-$C_1$ to $C_6$ alkylamino group, a $C_1$ to $C_6$ alkoxycarbonyl group, an optionally substituted aryl group, or an optionally substituted heteroaryl group, such that two residues chosen from R1, R2, and R3 and/or two residues chosen from R4, R5, and R6 can each form with one another and with the adjacent benzene ring a fused aromatic or heteroaromatic five- or six-membered cycle.

DETAILED DESCRIPTION OF THE INVENTION

"Keratinic fibers" (or also "keratin fibers") are understood in this context as furs, wool, feathers, and in particular human hair. Although agents according to the present invention are suitable chiefly for lightening keratinic fibers, there is in principle nothing standing in the way of use in other areas as well.

Agents according to the present invention contain the active substances in a cosmetic carrier. This cosmetic carrier is preferably aqueous, alcoholic, or aqueous alcoholic. For bleaching hair, such carriers include creams, emulsions, gels, or surfactant-containing foaming solutions (e.g., shampoos, foam aerosols, or other preparations suitable for use on the hair). It is also possible to make available for storage a powdered or tablet-form formulation, which is preferred for lightening agents. This is then mixed before use in an aqueous solvent or with organic solvents or with mixtures of water and organic solvents to obtain the utilization mixture. An "aqueous" carrier contains, for purposes of the invention, at least 40 wt %, particularly at least 50 wt % water. "Aqueous alcoholic" carriers are, for purposes of the present invention, aqueous compositions containing 3 to 70 wt % of a $C_1$ to $C_4$ alcohol, particularly ethanol or isopropanol. Agents according to the present invention can additionally contain further organic solvents such as 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred in this context. Preferred agents according to the present invention additionally contain a non-aqueous solvent. Preferred agents contain the solvent at a concentration from 0.1 to 30 wt %, preferably from 1 to 20 wt %, very particularly preferably from 2 to 10 wt %, based on the agent.

Hydrogen peroxide and/or a solid addition product thereof with organic or inorganic compounds is present in the agent according to the present invention as a first ingredient. In a preferred embodiment, hydrogen peroxide itself is used as an aqueous solution. Hydrogen peroxide can, however, also be used in the form of a solid addition compound of hydrogen peroxide with inorganic or organic compounds, for example, sodium perborate, sodium percarbonate, magnesium percarbonate, sodium percarbamide, polyvinylpyrrolidinone n $H_2O_2$ (where n is a positive integer greater than 0), urea peroxide, and melamine peroxide. In the latter case, the addition compounds release hydrogen peroxide in the application mixture according to the present invention (i.e., the agents contain free hydrogen peroxide in addition to the addition compound in the cosmetic carrier).

Preferably, hydrogen peroxide is metered into the agent according to the present invention as an aqueous hydrogen peroxide solution. An embodiment of the first subject of the invention is therefore one wherein the agent contains, as an oxidizing agent, hydrogen peroxide as an aqueous solution.

The concentration of a hydrogen peroxide solution is determined by regulatory provisions and by the desired effect; preferably, 6 to 12 wt % solutions in water are used. Preferred agents according to the present invention contain, based on their total weight, 0.01 to 12 wt %, preferably 0.1 to 10 wt %, more preferably 1 to 6 wt % hydrogen peroxide (calculated as 100% $H_2O_2$).

The agents contain at least one sulfonimine of formula (I) as a further ingredient. Examples of residues recited as substituents for compounds of formula (I) are listed below: examples of halogen atoms are fluorine, chlorine, bromine, and iodine. Examples of $C_1$ to $C_6$ alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, preferably methyl and ethyl. Examples of partly or entirely halogenated $C_1$ to $C_6$ alkyl residues are —$CH_2F$, —$CH_2Cl$, —$CF_3$, —$CH_2CF_3$, —$CF_2CF_3$, or —$CH(CF_3)_2$, particularly —$CF_3$. Examples of a $C_2$ to $C_6$ alkenyl group are prop-2-enyl (allyl), 2-methyl-prop-2-enyl, but-3-enyl, but-2-enyl, pent-4-enyl, or pent-3-enyl, preferably prop-2-enyl; examples of a $C_2$ to $C_6$ hydroxyalkyl group are —$CH_2CH_2OH$, —$CH_2CH_2CH_2OH$, —$CH_2CH(OH)CH_3$, —$CH_2CH_2CH_2CH_2OH$, particularly —$CH_2CH_2OH$. Examples of suitable $C_2$ to $C_6$ polyhydroxyalkyl groups are —$CH(OH)CH_2OH$, —$CH_2CH(OH)CH_2OH$, $CH(OH)CH(OH)CH_3$, —$CH_2CH_2CH(OH)CH_2OH$, preferably —$CH_2CH(OH)CH_2OH$. Examples of $C_1$ to $C_6$ alkoxy groups are the groups —$OCH_3$, —$OCH_2CH_3$, —$OCH(CH_3)_2$, —$OC(CH_3)_3$, preferably —$OCH_3$. Examples of $C_1$ to $C_6$ alkoxy-$C_2$ to $C_6$ alkyl groups are the groups —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$. Examples of a di-$C_1$ to $C_6$ alkylamino group are —$N(CH_3)_2$, —$N(CH_2CH_3)_2$, —$N(CH_2CH_2CH_3)_2$, —$N(CH_2CH_3)CH_3$, —$N(CH_3)[CH(CH_3)_2]$. Examples of a mono-$C_1$ to $C_6$ alkylamino group are —$NH(CH_3)$, —$NH(CH_2CH_3)$, —$NH(CH_2CH_2CH_3)$, —$NH\{C(CH_3)\}_3$, —$NH\{CH(CH_3)_2\}$. Examples of a $C_1$ to $C_6$ alkoxycarbonyl group are —$CO_2CH_3$, —$CO_2CH_2CH_3$, —$CO_2CH(CH_3)_2$, —$CO_2C(CH_3)_3$; examples of aryl-$C_1$ to $C_6$ alkyl groups are benzyl and 2-phenylethyl. Examples of an aryl group are phenyl, 1-naphthyl, or 2-naphthyl. Examples of a heteroaryl group are pyridin-2-yl, pyridin-3-yl, pyridin-4-yl, pyrimidin-2-yl, pyrrol-1-yl, pyrrol-2-yl, pyrrol-3-yl, pyrazol-1-yl, pyrazol-3-yl, or pyrazol-4-yl.

Compounds according to formula (I) wherein at least one of the residues chosen from R1, R2, and R3 and/or from R4, R5, R6 is a hydrogen atom are preferably suitable.

An embodiment of the present invention therefore contains as a sulfonimine in accordance with formula (I) at least one compound wherein at least one of the residues chosen from R1, R2, and R3 and/or from R4, R5, R6 is a hydrogen atom.

A further embodiment of the present invention contains as a sulfonimine in accordance with formula (I) at least one compound wherein at least one of the residues chosen from R1, R2, and R3 and/or from R4, R5, and R6 is a hydroxy group, a $C_1$ to $C_6$ alkoxy group, a halogen atom, a nitro group, or a carboxylic acid group.

Particularly preferred compounds of formula (I) are chosen from compounds 1 to 55 according to Table 1, with the relative position of the substituents R1 to R6 on the two benzene rings of the sulfonimine being determined by the fact that the carbon atoms adjacent to the sulfonimine are chosen as a reference atom numbered 1, and the benzene rings are sequentially numbered accordingly:

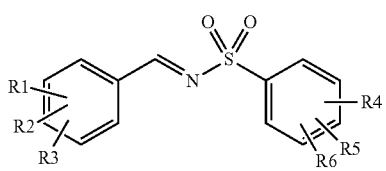

TABLE 1

| No. | Compounds of formula (I) | R1 | R2 | R3 | R4 | R5 | R6 |
|---|---|---|---|---|---|---|---|
| 1 | N-(phenylmethylidene)benzenesulfonamide | H | H | H | H | H | H |
| 2 | N-[(4-chlorophenyl)methylidene]benzenesulfonamide | 4-Cl | H | H | H | H | H |
| 3 | 4-chloro-N-(phenylmethylidene)benzenesulfonamide | H | H | H | 4-Cl | H | H |
| 4 | 4-chloro-N-([4-chlorophenyl)methylidene]benzenesulfonamide | 4-Cl | H | H | 4-Cl | H | H |
| 5 | 4-{[(phenylsulfonyl)imino]methylidene}benzoic acid | 4-$CO_2$H | H | H | H | H | H |
| 6 | 4-{[(phenylmethylidene)amino]sulfonyl}benzoic acid | H | H | H | 4-$CO_2$H | H | H |
| 7 | 4-({[(4-carboxyphenyl)methylidene]amino}sulfonyl)benzoic acid | 4-$CO_2$H | H | H | 4-$CO_2$H | H | H |
| 8 | N-[(4-methylphenyl)methylidene]benzenesulfonamide | 4-$CH_3$ | H | H | H | H | H |
| 9 | 4-methyl-N-(phenylmethylidene)benzenesulfonamide | H | H | H | 4-$CH_3$ | H | H |
| 10 | 4-methyl-N-[(4-methylphenyl)methylidene]benzenesulfonamide | 4-$CH_3$ | H | H | 4-$CH_3$ | H | H |
| 11 | N-[(4-hydroxyphenyl)methylidene]benzenesulfonamide | 4-OH | H | H | H | H | H |
| 12 | 4-hydroxy-N-[(phenylmethylidene)benzenesulfonamide | H | H | H | 4-OH | H | H |
| 13 | 4-hydroxy-N-[(4-hydroxyphenyl)methylidene]benzenesulfonamide | 4-OH | H | H | 4-OH | H | H |
| 14 | N-[(4-methoxyphenyl)methylidene]benzenesulfonamide | 4-$OCH_3$ | H | H | H | H | H |
| 15 | 4-methoxy-N-(phenylmethylidene)benzenesulfonamide | H | H | H | 4-$OCH_3$ | H | H |
| 16 | 4-methoxy-N-[(4-methoxyphenyl)methylidene]benzenesulfonamide | 4-$OCH_3$ | H | H | 4-$OCH_3$ | H | H |
| 17 | N-[(4-nitrophenyl)methylidene]benzenesulfonamide | 4-$NO_2$ | H | H | H | H | H |
| 18 | 4-nitro-N-(phenylmethylidene)benzenesulfonamide | H | H | H | 4-$NO_2$ | H | H |
| 19 | 4-nitro-N-[(4-nitrophenyl)methylidene]benzenesulfonamide | 4-$NO_2$ | H | H | 4-$NO_2$ | H | H |
| 20 | 4-({[(4-chlorophenyl)methylidene]amino}sulfonyl)benzoic acid | 4-Cl | H | H | 4-$CO_2$H | H | H |
| 21 | 4-({[(4-chlorophenyl)sulfonyl]imino}methyl)benzoic acid | 4-$CO_2$H | H | H | 4-Cl | H | H |
| 22 | 4-({[(4-bromophenyl)methylidene]amino}sulfonyl)benzoic acid | 4-Br | H | H | 4-$CO_2$H | H | H |
| 23 | 4-({[(4-bromophenyl)sulfonyl]imino}methyl)benzoic acid | 4-$CO_2$H | H | H | 4-Br | H | H |
| 24 | 4-({[(4-methoxyphenyl)methylidene]amino}sulfonyl)benzoic acid | 4-$CO_2$H | H | H | 4-$CO_2$H | H | H |
| 25 | 4-({[(4-methoxyphenyl)sulfonyl]imino}methyl)benzoic acid | 4-$CO_2$H | H | H | 4-$OC_3$H | H | H |
| 26 | N-[(4-methoxyphenyl(methylidene]-4-nitrobenzenesulfonamide | 4-$OC_3$H | H | H | 4-$NO_2$ | H | H |
| 27 | 4-methoxy-N-[(4-nitrophenyl)methylidene]benzenesulfonamide | 4-$NO_2$ | H | H | 4-$OCH_3$ | H | H |
| 28 | 4-chloro-N-[(4-nitrophenyl)methylidene]benzenesulfonamide | 4-Cl | H | H | 4-$NO_2$ | H | H |
| 29 | N-[(4-chlorophenyl)methylidene]-4-nitrobenzenesulfonamide | 4-$NO_2$ | H | H | 4-Cl | H | H |
| 30 | 4-bromo-N-[(4-nitrophenyl)methylidene]benzenesulfonamide | 4-Br | H | H | 4-$NO_2$ | H | H |
| 31 | N-[(4-bromophenyl)methylidene]-4-nitrobenzenesulfonamide | 4-$NO_2$ | H | H | 4-Br | H | H |
| 32 | 4-({[(4-nitrophenyl)methylidene]amino}sulfonyl)benzoic acid | 4-$NO_2$ | H | H | 4-$CO_2$H | H | H |
| 33 | 4-({[(4-nitrophenyl)sulfonyl]imino}methyl)benzoic acid | 4-$CO_2$H | H | H | 4-$NO_2$ | H | H |
| 34 | 2-chloro-4-{[(phenylsulfonyl)imino]methyl}benzoic acid | 3-Cl | 4-$CO_2$H | H | H | H | H |
| 35 | 2-chloro-4-{[(phenylmethylidene)amino]sulfonyl}benzoic acid | H | H | H | 3-Cl | 4-$CO_2$H | H |

TABLE 1-continued

| Compounds of No. formula (I) | R1 | R2 | R3 | R4 | R5 | R6 |
|---|---|---|---|---|---|---|
| 36 2-chloro-5-{[(phenylsulfonyl)imino]methyl}benzoic acid | 3-CO$_2$H | 4-Cl | H | H | H | H |
| 37 2-chloro-5-{[(phenylmethylidene)amino]sulfonyl}benzoic acid | H | H | H | 3-CO$_2$H | 4-Cl | H |
| 38 N-[(4-hydroxy-3-methoxyphenyl)methylidene]benzenesulfonamide | 3-OCH$_3$ | 4-OH | H | H | H | H |
| 39 4-hydroxy-3-methoxy-N-(phenylmethylidene)benzenesulfonamide | H | H | H | 3-OCH$_3$ | 4-OH | H |
| 40 4-chloro-[(4-hydroxy-3-methoxyphenyl)methylidene]benzenesulfonamide | 3-OCH$_3$ | 4-OH | H | 4-Cl | H | H |
| 41 N-[(4-chlorophenyl)methylidene]-4-hydroxy-3-methoxybenzenesulfonamide | 4-Cl | H | H | 3-OCH$_3$ | 4-OH | H |
| 42 4-({[(4-hydroxy-3-methoxyphenyl)methylidene]amino}sulfonyl)benzoic acid | 3-OCH$_3$ | 4-OH | H | 4-CO$_2$H | H | H |
| 43 4-({[(4-hydroxy-3-methoxyphenyl)sulfonyl]imino}methyl)benzoic acid | 4-CO$_2$H | H | H | 3-OCH$_3$ | 4-OH | H |
| 44 N-[(4-hydroxy-4-methoxyphenyl)methylidene]benzenesulfonamide | 2-OCH$_3$ | 4-OH | H | H | H | H |
| 45 4-hydroxy-2-methoxy-N-(phenylmethylidene)benzenesulfonamide | H | H | H | 2-OCH$_3$ | 4-OH | H |
| 46 4-chloro-[(4-hydroxy-2-methoxyphenyl)methylidene]benzenesulfonamide | 2-OCH$_3$ | 4-OH | H | 4-Cl | H | H |
| 47 N-[(4-chlorophenyl)methylidene]-4-hydroxy-2-methoxybenzenesulfonamide | 4-Cl | H | H | 2-OCH$_3$ | 4-OH | H |
| 48 4-({[(4-hydroxy-2-methoxyphenyl)methylidene]amino}sulfonyl)benzoic acid | 2-OCH$_3$ | 4-OH | H | 4-CO$_2$H | H | H |
| 49 4-({[(4-hydroxy-2-methoxyphenyl)sulfonyl]imino}methyl)benzoic acid | 4-CO$_2$H | H | H | 2-OCH$_3$ | 4-OH | H |
| 50 4-({[(4-carboxy-3-chlorophenyl)methylidene]amino}sulfonyl)-2-chlorobenzoic acid | 3-Cl | 4-CO$_2$H | H | 3-Cl | 4-CO$_2$H | H |
| 51 5-({[(3-carboxy-4-chlorophenyl)methylidene]amino}sulfonyl)-2-chlorobenzoic acid | 3-CO$_2$H | 4-Cl | H | 3-CO$_2$H | 4-Cl | H |
| 52 4-hydroxy-N-[(4-hydroxy-3-methoxyphenyl)methylidene]-3-methoxybenzenesulfonamide | 3-OCH$_3$ | 4-OH | H | 3-OCH$_3$ | 4-OH | H |
| 53 4-hydroxy-N-[(4-hydroxy-2-methoxyphenyl)methylidene]-3-methoxybenzenesulfonamide | 2-OCH$_3$ | 4-OH | H | 2-OCH$_3$ | 4-OH | H |
| 54 4-chloro-N-[(4-methoxyphenyl)methylidene]benzenesulfonamide | 4-OCH$_3$ | H | H | 4-Cl | H | H |
| 55 N-[(4-chlorophenyl)methylidene]-4-methoxybenzenesulfonamide | 4-Cl | H | H | 4-OCH$_3$ | H | H |

Preferred agents in this context contain in a cosmetic carrier, alongside at least one oxidizing agent chosen from hydrogen peroxide and/or a solid addition product thereof with organic or inorganic compounds, at least one compound chosen from N-(phenylmethylidene)benzenesulfonamide, N-[(4-chloro-phenyl)methylidene]benzenesulfonamide, 4-chloro-N-(phenylmethylidene)benzenesulfonamide, 4-{[(phenylsulfonyl)imino]methylidene}benzoic acid, 4-{[(phenylmethylidene)amino]sulfonyl}benzoic acid, N-[(4-methylphenyl)methylidene]benzenesulfonamide, 4-methyl-N-(phenylmethylidene)benzenesulfonamide, N-[(4-hydroxyphenyl)methylidene]benzenesulfonamide, 4-hydroxy-N-[(phenylmethylidene)benzenesulfonamide, N-[(4-methoxyphenyl)methylidene]benzenesulfonamide, 4-methoxy-N-(phenylmethylidene)benzenesulfonamide, N-[(4-nitro-phenyl)methylidene]benzenesulfonamide, 4-nitro-N-(phenylmethylidene)benzenesulfonamide, 4-({[(4-chlorophenyl)methylidene]amino}sulfonyl)benzoic acid, 4-({[(4-chlorophenyl)sulfonyl]imino}methyl)benzoic acid, N-[(4-hydroxy-3-methoxyphenyl)methylidene]benzenesulfonamide, 4-chloro-[(4-hydroxy-3-methoxyphenyl)methylidene]benzenesulfonamide, 4-({[(4-hydroxy-3-methoxyphenyl)methylidene]amino}sulfonyl)benzoic acid, N-[(4-hydroxy-2-methoxyphenyl)methylidene]benzenesulfonamide, 4-chloro-[(4-hydroxy-2-methoxyphenyl)methylidene]benzenesulfonamide, 4-({[(4-hydroxy-2-methoxyphenyl)methylidene]amino}sulfonyl) benzoic acid, and 4-chloro-N-[(4-methoxyphenyl) methylidene]benzenesulfonamide.

In a preferred embodiment of the first subject of the invention, the agent contains as a sulfonimine according to formula (I) at least N-[(4-methoxyphenyl)methylidene]benzenesulfonamide.

Agents according to the present invention preferably contain sulfonimine(s) of formula (I) in an amount of from 0.01 to 25 wt %, particularly 0.1 to 10 wt %, and more particularly 0.5 to 5.0 wt %, based on total weight of the ready-to-use agent.

Agents according to the present invention can also be produced directly before use from two or more separately packaged preparations. This is particularly appropriate for separating incompatible ingredients in order to prevent premature reaction. One usual approach is therefore to mix directly before use a first agent containing at least one sulfonimine of general formula (I) with a second agent containing the oxidizing agent(s) according to the present invention.

A further subject of the present invention is an agent for lightening keratinic fibers, particularly human hair, that is obtained immediately before application onto the hair from a flowable preparation (A) containing a sulfonimine of general formula (I) and an oxidizing agent preparation (B) containing at least one oxidizing agent chosen from hydrogen peroxide and/or addition products thereof with organic or inorganic compounds.

Oxidizing agent preparation (B) is preferably an aqueous, flowable oxidizing agent preparation. Preferred agents according to the present invention for lightening keratinic fibers are characterized in that the flowable oxidizing agent preparation (B) contains, based on its weight, 40 to 90 wt %, preferably 50 to 85 wt %, more preferably 55 to 80 wt %, even more preferably 60 to 77.5 wt %, and particularly 65 to 75 wt % water.

Use of the sulfonimine according to formula (I) considerably increases the lightening performance of agents according to the present invention so that in some circumstances it is possible to dispense with the use of further bleaching power intensifiers, resulting in reduced hair damage.

For particularly intense lightening operations, particularly for very dark, highly pigmented initial hair colors, however, it may be necessary to incorporate additional bleaching power intensifiers into the agent. If an intense lightening result of this kind is desired, it is then preferred according to the present invention if a hair-bleaching preparation (C) containing at least one bleaching power intensifier is additionally mixed into the mixture of oxidizing agent preparation (B) and preparation (A).

It may be immaterial in this context whether a mixture of (A) and (B) is first produced and then the hair-bleaching preparation (C) is mixed in, or whether the sequence used for mixing the individual components is different therefrom. It is preferred to mix the individual preparations in a sequence as close together in time as possible, and to apply the ready-to-use agent preferably quasi-synchronously onto the keratinic fibers.

A further embodiment of the present invention is therefore an agent for bleaching keratinic fibers produced by mixing at least one oxidizing agent preparation (B) containing at least one oxidizing agent chosen from hydrogen peroxide and addition compounds thereof on solid carriers, at least one hair-bleaching preparation (C) containing at least one bleaching power intensifier, and at least one preparation (A), preparation (A) containing, in a cosmetic carrier, at least one sulfonimine according to formula (I).

In the context of this invention, peroxo compounds can be used as additional bleaching power intensifiers of hair-bleaching preparation (C), as well as compounds that yield aliphatic peroxocarboxylic acids and/or substituted perbenzoic acid under perhydrolysis conditions, carbonic acid derivatives, alkyl carbonates, alkyl carbamates, silyl carbonates and silyl carbamates.

The bleaching power intensifier is preferably chosen from ammonium peroxodisulfate, alkali metal peroxodisulfates, ammonium peroxomonosulfate, alkali metal hydrogen peroxomonosulfates, alkali metal peroxodiphosphates, and alkaline earth metal peroxides. Particularly preferred bleaching power intensifiers are ammonium peroxodisulfate, potassium peroxodisulfate, sodium peroxodisulfate, potassium hydrogen peroxomonosulfate, potassium peroxodiphosphate, magnesium peroxide, and barium peroxide.

Agents that contain as a bleaching power intensifier in hair-bleaching preparation (C) at least one inorganic salt selected from peroxomonosulfates and/or peroxodisulfates, are particularly preferred according to the present invention. It has also proven, in the context of work on the present invention, to be particularly preferred if the agents according to the present invention contain at least two different peroxodisulfates. Preferred peroxodisulfate salts in this context are combinations of ammonium peroxodisulfate and potassium peroxodisulfate and/or sodium peroxodisulfate.

In a further embodiment of this invention, the lightening agent additionally contains at least one inorganic persulfate salt or peroxodisulfate salt, particularly ammonium peroxodisulfate, potassium peroxodisulfate, and/or sodium peroxodisulfate.

The peroxo compounds are present in an amount of from 0.1 to 25 wt %, particularly 0.5 to 15 wt %, based on total weight of the ready-to-use agent.

Persulfate salts or peroxodisulfate salts can be used in the form of an optionally dust-filtered powder, a paste, or a mold-pressed shaped element.

Anhydrous compositions according to the present invention can contain a further bleaching power intensifier instead of and/or in addition to the solid peroxo compounds.

Compounds that, under perhydrolysis conditions, yield aliphatic peroxocarboxylic acids preferably having 1 to 10 carbon atoms, particularly 2 to 4 carbon atoms, and/or optionally substituted perbenzoic acid, can be used as bleach intensifiers. Substances that carry O- and/or N-acyl groups having the aforesaid number of carbon atoms and/or optionally substituted benzoyl groups are suitable. Multiply acylated alkylenediamines, particularly tetraacetylethylenediamine (TAED), acylated triazine derivatives, particularly 1,5-diacetyl-2,4-dioxohexahydro-1,3,5-triazine (DADHT), acylated glycolurils, particularly tetraacetyl glycoluril (TAGU), N-acylimides, particularly N-nonanoyl succinimide (NOSI), acylated phenolsulfonates, particularly n-nonanoyl or isononanoyl oxybenzenesulfonate (n- or iso-NOBS), carboxylic acid anhydrides, particularly phthalic acid anhydride, acylated polyvalent alcohols, particularly triacetin, ethylene glycol diacetate, and 2,5-diacetoxy-2,5-dihydrofuran, are preferred.

In preferred fashion, carbonate salts or hydrogen carbonate salts can be used as bleach intensifiers of the carbonic-acid derivative type. These are preferably chosen from ammonium, alkali-metal (particularly potassium and sodium), and alkaline-earth metal (particularly magnesium and calcium) carbonate salts or hydrogen carbonate salts. Particularly preferred carbonate or hydrogen carbonate salts are ammonium hydrogen carbonate, ammonium carbonate, sodium hydrogen carbonate, sodium carbonate, potassium hydrogen carbonate, potassium carbonate, magnesium carbonate, and calcium carbonate. These preferred salts can be used as bleach intensifiers alone or in mixtures of at least two representatives thereof.

Alkyl carbonate, alkyl carbamate, and silyl carbonate, and silyl carbamate bleach intensifiers can be used as bleach intensifiers in the anhydrous compositions.

At least one compound chosen from acetic acid, lactic acid, tartaric acid, citric acid, salicylic acid, and orthophthalic acid can preferably be present in compositions according to the present invention as further additional bleach intensifiers.

Bleaching power intensifiers used in addition to or instead of peroxo compounds are present in cosmetic agents according to the present invention preferably in amounts from 0.05 to 10 wt %, particularly 0.2 to 5 wt %, based on total weight of the ready-to-use agent.

Although in principle no limitations exist regarding the formulation of the hair-bleaching preparation (C), it is preferred according to the present invention if preparation (C) is formulated in anhydrous fashion.

"Anhydrous" means, for purposes of the present invention, a water content, based on preparation (C), of 5 wt % or less, particularly 2 wt % or less. Hair-bleaching preparations containing 0.1 wt % or less of water can be very particularly preferred according to the present invention. Preparation (C) is preferably formulated anhydrously as a powder or as a paste.

For anhydrous formulations, it is particularly preferred if preparation (C) contains at least one non-hydroxylated fatty acid ester having a melting point of at most 50° C., particularly at most 30° C., and/or at least one $C_{10}$ to $C_{30}$ fatty acid having at least one additional hydroxy group and/or a derivative thereof. Esters of non-hydroxylated $C_6$ to $C_{30}$ alkylmonocarboxylic acids with $C_2$ to $C_{30}$ monoalcohols are preferred according to the present invention as fatty acid esters. Isopropyl myristate, isononanoic acid cetearyl esters, 2-ethylhexyl palmitate, stearic acid 2-ethylhexyl ester, cetyl oleate, coconut fatty alcohol caprinate/caprylate, n-butyl stearate, oleyl erucate, isopropyl palmitate, oleyl oleate, lauric acid hexyl ester, myristyl myristate, cetearyl isononanoate, oleic acid decyl ester are particularly preferred according to the present invention.

Hair-bleaching processes on keratin fibers usually proceed in an alkaline environment. However, in order to minimize stress on both the keratin fibers and the skin, it is not desirable to have too high a pH. It is therefore preferred if the pH of the ready-to-use agent is from 7 to 11, particularly from 8 to 10.5. The pH values for purposes of the present invention are pH values that have been measured at a temperature of 22° C.

Alkalizing agents usable according to the present invention for establishing the preferred pH can be chosen from ammonia, alkanolamines, basic amino acids, and inorganic alkalizing agents such as alkali/alkaline-earth metal hydroxides, alkali/alkaline-earth metal silicates, alkali/alkaline-earth metal phosphates, and alkali/alkaline-earth metal hydrogen phosphates. Lithium, sodium, and/or potassium preferably serve as metal ions.

Particularly preferred alkanolamines are monoethanolamine and triethanolamine. The alkanolamines are preferably present in an amount of from 0.05 to 10 wt %, particularly 0.5 to 5 wt %, based on total weight of the ready-to-use agent.

Basic amino acids usable as alkalizing agents according to the present invention are preferably chosen from L-arginine, D-arginine, D/L-arginine, L-lysine, D-lysine, D/L-lysine, L-ornithine, D-ornithine, D/L-ornithine, L-histidine, D-histidine, and D/L-histidine. More preferably, L-arginine, D-arginine, D/L-arginine are used as an alkalizing agent for purposes of the invention.

It has been discovered that agents also preferred according to the present invention additionally contain an organic alkalizing agent. In an embodiment of the first subject of the invention, the agent additionally contains at least one alkalizing agent chosen from ammonia, alkanolamines, and basic amino acids, particularly from ammonia, monoethanolamine, and arginine or compatible salts thereof.

It has been discovered that the hair-bleaching performance of the agents can be further enhanced if the hair-bleaching agents contain at least one aromatic organic solvent. Aromatic solvents for purposes of the invention are those compounds having an aromatic structural unit (e.g., a phenyl group) in their structural formula, and furthermore are liquid under standard conditions (i.e., at room temperature and standard pressure). These are preferably carbocyclic solvents that preferably also carry a hydroxy group. Preferred examples of such aromatic solvents are alcohols such as benzyl alcohol, 2-phenylethyl alcohol, 1-phenylethyl alcohol, 2-phenoxyethanol, 3-methylbenzyl alcohol, 2-methoxybenzyl alcohol, and 3-methoxybenzyl alcohol.

An aromatic solvent very particularly preferred according to the present invention is benzyl alcohol. Preferred agents according to the present invention contain 0.01 to 15 wt %, particularly 0.1 to 10 wt %, and more particularly 0.5 to 5.0 wt %, based on total weight of the ready-to-use agent, of at least one aromatic organic solvent.

It is furthermore advantageous if the lightening agents contain at least one stabilizer or complexing agent. Particularly preferred stabilizers are phenacetin, alkali benzoates (sodium benzoate) and salicylic acid. All complexing agents of the existing art can also be used. These can belong to various chemical groups, and preferably are used individually or in a mixture with one another. Preferred complexing agents include nitrogen-containing polycarboxylic acids, particularly EDTA, and phosphonates, preferably hydroxyalkane- or aminoalkanephosphonates and particularly 1-hydroxyethane-1,1-diphosphonate (HEDP) or the di- or tetrasodium salt thereof, and/or ethylenediaminetetramethylenephosphonate (EDTMP) or the hexasodium salt thereof, and/or diethylenetriaminepentamethylenephosphonate (DTPMP) or the hepta- or octasodium salt thereof.

The ready-to-use lightening agents can also contain additional active substances, adjuvants, and additives.

The ready-to-use lightening agents are preferably available as a flowable preparation with an emulsifier or a surfactant additionally added to it. Surface-active substances are referred to as "surfactants" or as "emulsifiers" depending on the application sector, and are chosen from anionic, cationic, zwitterionic, amphoteric, and nonionic surfactants and emulsifiers.

Preferred agents according to the present invention additionally contain at least one anionic surfactant. Preferred anionic surfactants are fatty acids, alkyl sulfates, alkyl ether sulfates, and ethercarboxylic acids having 10 to 20 carbon atoms in the alkyl group and up to 16 glycol ether groups in the molecule. Anionic surfactants are used in amounts from 0.1 to 45 wt %, preferably 1 to 30 wt %, and very preferably from 1 to 15 wt %, based on total weight of the ready-to-use agent. Preferred agents additionally contain at least one zwitterionic surfactant. Particularly suitable zwitterionic surfactants are betaines and N-alkyl-N,N-dimethylammonium glycinates, N-acylaminopropyl-N,N-dimethylammonium glycinates, and 2-alkyl-3-carboxymethyl-3-hydroxyethylimidazolines. A preferred zwitterionic surfactant is the fatty acid amide derivative known by the INCI name Cocamidopropyl Betaine. Preferred agents according to the present invention additionally contain at least one amphoteric surfactant. Examples of suitable amphoteric surfactants are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids. Particularly preferred amphoteric surfactants are N-cocalkylaminopropionate, cocacylaminoethylaminopropionate, and $C_{12}$ to $C_{18}$ acyl sarcosine. It is furthermore advantageous if the agents contain further nonionogenic surface-active substances. Alkyl polyglycosides have proven successful as preferred nonionic surfactants, as well as alkylene oxide addition products with saturated linear fatty alcohols and fatty acids having in each case 2 to 30 mol ethylene oxide per mol fatty alcohol or fatty acid. The nonionic, zwitterionic, or amphoteric surfactants are used in amounts from 0.1 to 45 wt %, preferably 1 to 30 wt %, and very particularly preferably from 1 to 15 wt %, based on total weight of the ready-to-use agent.

Suitable agents according to the present invention can also contain quaternary ammonium compound, esterquat, and amidoamine cationic surfactants. Preferred quaternary ammonium compounds are ammonium halides, as well as the imidazolium compounds known by the INCI names Quaternium-27 and Quaternium-83. Further cationic surfactants usable according to the present invention are the quaternized protein hydrolysates. An amidoamine compound that is particularly suitable according to the present invention is the stearamidopropyldimethylamine available commercially under the designation Tegoamid® S 18. Preferred esterquats are quaternized ester salts of fatty acids with triethanolamine, quaternized ester salts of fatty acids with diethanol alkylamines, and quaternized ester salts of fatty acids with 1,2-dihydroxypropyldialkylamines. Such products are marketed, for example, under the trademarks Stepantex®, Dehyquart® and Armocare®. The cationic surfactants are preferably present in agents according to the present invention in amounts from 0.05 to 10 wt %, based on total agent. Quantities from 0.1 to 5 wt % are particularly preferred.

The ready-to-use lightening agents can contain further adjuvants and additives. For example, it has proven to be advantageous if the agents contain at least one thickening agent. No limitations exist in principle with regard to this thickening agent. Both organic and entirely inorganic thickening agents can be utilized.

Suitable thickening agents are anionic synthetic polymers; cationic synthetic polymers; naturally occurring thickening agents such as nonionic guar gums, scleroglucan gums or xanthan gums, gum arabic, ghatti gum, karaya gum, tragacanth gum, carrageenan gum, agar-agar, locust bean flour, pectins, alginates, starch fractions and derivatives such as amylose, amylopectin, and dextrins, as well as cellulose derivatives such as methyl cellulose, carboxyalkyl celluloses, and hydroxyalkyl celluloses; nonionic fully synthetic polymers, such as polyvinyl alcohols or polyvinylpyrrolidinone; and inorganic thickening agents, particularly sheet silicates such as bentonite, particularly smectites such as montmorillonite or hectorite.

To further enhance lightening, at least one $SiC_2$ compound such as silicic acid or silicates, particularly water glasses, can additionally be added to the composition according to the present invention. It may be preferred to use $SiO_2$ compounds in amounts from 0.05 wt % to 15 wt %, particularly from 0.15 wt % to 10 wt %, and very particularly from 0.2 wt % to 5 wt %, based on the anhydrous composition according to the present invention. The quantitative indications represent the concentration of $SiO_2$ compounds (without their water component) in the agents.

To suppress undesired residual color impressions, especially in the reddish or bluish region, the lightening agents can contain specific substantive dyes of the complementary colors. These are dyes that absorb directly onto the hair and do not require an oxidizing process in order to form the color. Substantive dyes are usually nitrophenylenediamines, nitroaminophenols, azo dyes, anthraquinones, or indophenols. Substantive dyes are known as anionic, cationic, and nonionic substantive dyes. The substantive dyes are respectively used preferably in an amount from 0.001 to 2 wt %, based on total utilization preparation.

Preferred anionic substantive dyes include compounds known under the international designations or commercial names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic substantive dyes are cationic triphenylmethane dyes such as Basic Blue 7, Basic Blue 26, Basic Violet 2, and Basic Violet 14, aromatic systems substituted with a quaternary nitrogen group, for example, Basic Yellow 57, Basic Red 76, Basic Blue 99, Basic Brown 16, and Basic Brown 17, cationic anthraquinone dyes such as HC Blue 16 (Bluequat B), as well as substantive dyes which contain a heterocycle having at least one quaternary nitrogen atom, particularly Basic Yellow 87, Basic Orange 31, and Basic Red 51. Cationic substantive dyes marketed under the Arianor trademark are likewise preferred cationic substantive dyes according to the present invention. Nonionic nitro and quinone dyes and neutral azo dyes are particularly suitable as nonionic substantive dyes. Preferred nonionic substantive dyes are compounds known under the international designations or commercial names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol. Lightening agents having at least one combination of tetrabromophenol blue and Acid Red 92 are very particularly preferred.

Agents according to the present invention can additionally contain further active substances, adjuvants, and additives such as nonionic polymers; additional silicones such as dimethicones or cyclomethicones, amodimethicones, dimethicone polyols; cationic polymers; zwitterionic and amphoteric polymers; anionic polymers; structuring agents such as glucose, maleic acid, and lactic acid, hair-conditioning compounds; perfume oils, dimethylisosorbide, and cyclodextrins; fiber-structure-improving active substances, particularly mono-, di- and oligosaccharides; dyes for coloring the agent; anti-dandruff active substances; amino acids and oligopeptides, particularly arginine and/or serine; animal- and/or vegetable-based protein hydrolysates; vegetable oils; light-protection agents such as derivatized benzophenones, cinnamic acid derivatives, and triazines; active substances such as panthenol, pantothenic acid, pantolactone, allantoin, pyrrolidinonecarboxylic acids, and salts thereof, as well as bisabolol; polyphenols, particularly hydroxycinnamic acids, 6,7-dihydroxycumarins, hydroxybenzoic acids, catechins, tannins, leucoanthocyanidines, anthocyanidines, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration substances such as glycerol, propylene glycol monoethyl ether, carbonates, hydrogen carbonates, guanidines, ureas, and primary, secondary, and tertiary phosphates; opacifiers; luster agents; pigments, and propellants such as propane/butane mixtures, $N_2O$, dimethyl ether, $CO_2$, and air.

One skilled in the art will arrive at a selection of these further substances according to the desired properties of the agents. Regarding further optional components as well as the quantities of those components used, reference is made expressly to the relevant manuals known to one skilled in the art (e.g., Kh. Schrader, Grundlagen and Rezepturen der Kosmetika [Cosmetics fundamentals and formulations], 2nd Ed., Huthig Buch Verlag, Heidelberg (1989)). Additional active substances and adjuvants are used in agents according to the present invention preferably in amounts from 0.0001 to 10 wt %, particularly 0.0005 to 5 wt %, based on total weight of the utilization mixture.

A further subject of the present invention is a method for lightening keratinic fibers, particularly human hair, comprising applying onto the keratin-containing fibers an agent containing, in a cosmetic carrier—
(i) at least one oxidizing agent selected from hydrogen peroxide and/or a solid addition product thereof with organic or inorganic compounds, and
(ii) at least one sulfonimine of formula (I)

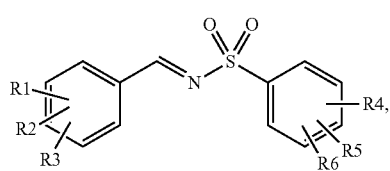

wherein
R1 to R6 are each, mutually independently, a hydrogen atom, a halogen atom, a $C_1$ to $C_6$ alkyl group, a partly or entirely halogenated $C_1$ to $C_6$ alkyl group, a $C_2$ to $C_6$ alkenyl group, a $C_1$ to $C_6$ hydroxyalkyl group, a $C_2$ to $C_6$ polyhydroxyalkyl group, a $C_1$ to $C_6$ alkoxy group, a $C_1$ to $C_6$ alkoxy-$C_2$ to $C_6$ alkyl group, an aryl-$C_1$ to $C_6$ alkyl group, a hydroxy group, a nitrile group, a nitro group, a carboxylic acid group, a sulfonic acid group, a sulfonamido group, an amino group, a di-$C_1$ to $C_6$ alkylamino group, a mono-$C_1$ to $C_6$ alkylamino group, a $C_1$ to $C_6$ alkoxycarbonyl group, an optionally substituted aryl group, or an optionally substituted heteroaryl group, such that two residues chosen from R1, R2, and R3 and/or two residues chosen from R4, R5, and R6 can each form with one another and with the adjacent benzene ring a fused aromatic or heteroaromatic five- or six-membered cycle,
leaving the agent on the fibers for 5 to 60 minutes, and then rinsing out the agent again or washing out the agent again with a shampoo.

The contact time of the ready-to-use lightening agent is preferably from 5 to 45 minutes, particularly 10 to 40 minutes, and more particularly 15 to 35 minutes. During the contact time of the agent on the fibers, it may be advantageous to assist the lightening operation by providing heat. Heat can be provided from an external heat source such as warm air from a warm air blower, and also, particularly in the case of a hair lightening process on living subjects, from the body temperature of the subject. In the latter option, the portion to be lightened is usually covered with a hood. A contact phase at room temperature is likewise according to the present invention. Temperature during contact time is particularly from 20° C. to 40° C., more particularly from 25° C. to 38° C. The oxidative coloring agents already produce good hair-bleaching and lightening results at physiologically acceptable temperatures of 45° C. or less.

After the contact time has ended, the remaining lightening preparation is rinsed out of the hair with water or with a cleaning agent. A commercial shampoo can serve as a cleaning agent in this context, or the cleaning agent can be omitted and the rinsing-out operation can occur using tap water if the lightening agent possesses a carrier with high surfactant content.

A further subject of the invention is the cosmetic use of an agent of the first subject of the invention to lighten keratin-containing fibers, particularly human hair.

The embodiments of the first subject of the invention apply, mutatis mutandis, to the method of the second subject of the invention and to the use of the third subject of the invention.

The packaging of lightening agents according to the present invention is not subject in principle to limitations of any kind. Agents according to the present invention are usually packaged as one-component agents (A) that, if applicable, are mixed immediately before utilization with a second preparation containing an oxidizing agent. It has, however, proven to be preferred if the product is packaged as a two-component agent. The two preparations are then mixed before use.

In order to prevent a premature, undesired reaction of the sulfonimines of general formula (I) with the oxidizing agent, sulfonimines of formula (I) are usefully packaged separately from the oxidizing agent preparation and brought into contact only immediately before use.

A further subject of the present invention is therefore an agent which is produced immediately before utilization by mixing at least two preparations, the at least two preparations being provided in at least two separately packaged containers, with one container containing an agent (A) comprising in a cosmetic carrier at least one sulfonimine of general formula (I), and a further container comprising an oxidizing agent preparation (B) having at least one oxidizing agent chosen from hydrogen peroxide and/or addition compounds thereof with organic or inorganic compounds.

In order to offer the components of the ready-to-use lightening agent to the consumer in as convenient a manner as possible, it is useful to market the individual preparations together in one packaging unit.

A further subject of the present invention is therefore a multi-component packaging unit ("kit of parts") for lightening keratinic fibers comprising, in containers packaged separately from one another, at least one oxidizing-agent preparation (B) containing hydrogen peroxide or a solid addition compound of hydrogen peroxide with inorganic or organic compounds, and at least one preparation (A) containing, in a cosmetic carrier, at least one sulfonimine of formula (I).

In order to enhance the lightening performance, the multi-component packaging unit can additionally contain at least one hair-bleaching preparation (C).

A further embodiment of this subject of the invention is therefore one wherein the kit of parts additionally contains, in a separately packaged container, at least one hair-bleaching powder (C) containing at least one inorganic peroxodisulfate salt chosen from ammonium peroxodisulfate, potassium peroxodisulfate, and/or sodium peroxodisulfate.

The components of the multi-package unit are packaged separately from one another in physically different containers. The term "container" represents in this context a receiving capability, regardless of its shape, material, or closure, which embodies the capability of containing substances or substance mixtures. The term "container" therefore includes, without being limited thereto, the interior of a tube, of a pouch or sack, of a canister, of a tin, of a pan, of a bottle, of a glass or a packet, of a carton, of a box, of an envelope, or of another receptacle. The containers can be equipped with a reclosable opening such as a screw closure. This may be advantageous particularly when multiple agents are to be intimately mixed with one another, for example, by shaking before use.

Components of the lightening preparation can be present in a double-chamber container having a separate or shared opening. It is preferred, however, to distribute them among different containers and to instruct the consumer to mix them with one another before utilization.

The multi-component packaging unit (kit of parts) preferably additionally contains a set of instructions for use. The instructions for use contain, in particular, information, explanations, and if applicable illustrations for the user (male/female) for utilizing the agents from the containers of the packaging unit in a method in accordance with the second subject of the invention. It may also be preferred if a mixing aid such as a dish, an application aid (e.g., a comb or brush), and/or personal protection equipment (e.g., disposable gloves) are included with the kit.

Regarding preferred embodiments of the multi-component packaging unit according to the present invention, the embodiments of the foregoing subjects of the invention apply mutatis mutandis.

EXAMPLES

1. Synthesis Examples

1.1 Synthesis of 4-{[(phenylsulfonyl)imino]methylidene}benzoic acid (activator 1)

An equimolar mixture of 25.0 g (0.17 mol) 4-carboxybenzaldehyde and 26.7 g (0.17 mol) benzenesulfonamide was placed into toluene. 100 mg p-toluenesulfonic acid was added as a catalyst. The mixture was then heated under reflux on a water separator until the theoretically calculated quantity of water had separated. After cooling to room temperature, the precipitated solid was filtered off and dried under vacuum. Yield: 45.7 g (94.8%); $^1$H-NMR (400 MHz, DMSO-$d_6$): δ [ppm]=7.59 (m, 2H); 7.78 (d, 1H); 8.02 (m, 2H); 8.12 (d, 2H); 8.18 (d, 2H); 9.30 (s, 1H); $^{13}$C-NMR (400 MHz, DMSO-d6): δ [ppm]=127.8; 129.7; 131.4; 134.1; 135.8; 136.0; 137.9; 166.5; 171.2; 192.9.

1.2 Synthesis of N-[(4-Methoxyphenyl)Methylidene]Benzenesulfonamide (Activator 2)

An equimolar mixture of 25.0 g (0.18 mol) 4-methoxybenzaldehyde and 28.3 g (0.18 mol) benzenesulfonamide was placed into toluene. 100 mg p-toluenesulfonic acid was added as a catalyst. The mixture was then heated under reflux on a water separator until the theoretically calculated quantity of water had separated. The reaction mixture was cooled first to room temperature and then in a refrigerator to 10° C. The precipitated solid was then filtered off and dried under vacuum. Yield: 37.6 g (74.3%); $^1$H-NMR (400 MHz, DMSO-$d_6$): δ [ppm]=7.13 (d, 2H); 7.69 (m, 2H); 7.77 (d, 1H); 7.96 (d, 2H); 8.04 (d, 2H); 9.11 (s, 1H); $^{13}$C-NMR (400 MHz, DMSO-d6): δ [ppm]=55.6; 114.7; 124.9; 127.5; 129.6; 133.8; 134.0; 138.8; 165.0; 170.8.

1.3 Synthesis of 4-({[(4-chlorophenyl)sulfonyl]imino}methyl)benzoic acid (Activator 3)

An equimolar mixture of 25.0 g (0.17 mol) 4-carboxybenzaldehyde and 32.6 g (0.17 mol) 4-chlorobenzenesulfonamide was placed into toluene. 100 mg p-toluenesulfonic acid was added as a catalyst. The mixture was then heated under reflux on a water separator until the theoretically calculated quantity of water had separated. After cooling to room temperature, the precipitated solid was filtered off and dried under vacuum. Yield: 48.3 g (89.4%); $^1$H-NMR (400 MHz, DMSO-$d_6$): δ [ppm]=7.78 (d, 2H); 8.09 (d, 2H); 8.11 (d, 2H); 8.23 (d, 2H); 9.29 (s, 1H); $^{13}$C-NMR (400 MHz, DMSO-d6): δ [ppm]=130.2; 130.5; 131.8; 135.5; 136.0; 136.1; 139.1; 166.6; 171.9; 193.0.

1.4 Synthesis of N-[(4-hydroxy-2-methoxyphenyl)methylidene]benzenesulfonamide (Activator 4)

An equimolar mixture of 27.4 g (0.18 mol) 4-hydroxy-2-methoxybenzaldehyde and 28.3 g (0.18 mol) benzenesulfonamide was placed into toluene. 100 mg p-toluenesulfonic acid was added as a catalyst. The mixture was then heated under reflux on a water separator until the theoretically calculated quantity of water had separated. After cooling to room temperature, the precipitated solid was filtered off and dried under vacuum. Yield: 43.0 g (78.9%).

1.5 Synthesis of 4-chloro-N-[(4-methoxyphenyl)methylidene]benzenesulfonamide (Activator 5)

An equimolar mixture of 25.0 g (0.18 mol) 4-methoxybenzaldehyde and 34.4 g (0.18 mol) 4-chlorobenzenesulfonamide was placed into toluene. 100 mg p-toluenesulfonic acid was added as a catalyst. The mixture was then heated under reflux on a water separator until the theoretically calculated quantity of water had separated. The reaction mixture was cooled first to room temperature and then in a refrigerator to 10° C. Because no solid had precipitated even after cooling in the refrigerator, the reaction mixture was completely concentrated in a rotary evaporator and the residue was dried under vacuum. Yield: 56.6 g (99.3%).

2. Hair-Bleaching Examples

Hair Bleaching with Hydrogen Peroxide

2.1. Production of a Hair-Bleaching Cream

Hair-bleaching creams were manufactured as follows, using the constituents listed:

|  | Wt % | |
| --- | --- | --- |
| Raw material | C1 | I1 |
| Hydrenol D | 12.00 | 12.00 |
| Lorol tech. | 2.40 | 2.40 |
| Texapon NSO | 26.50 | 26.50 |
| Stabylen 30 | 0.10 | 0.10 |
| Cetiol OE | 2.40 | 2.40 |
| Turpinal SL | 0.20 | 0.20 |
| Sodium silicate 40/42 | 0.50 | 0.50 |
| Ammonium sulfate | 1.00 | 1.00 |
| Ammonia, 25% | 7.60 | 7.60 |
| N-[(4-methoxyphenyl)methylidene]benzenesulfonamide (activator 2) | — | 2.00 |
| Water | to 100 | to 100 |

| | |
| --- | --- |
| Hydrenol ® D | INCI name: Cetearyl Alcohol (Cognis) |
| Lorol ® tech. | INCI name: Coconut Alcohol (Cognis) |
| Texapon ® NSO | approx. 27.5% active substance; INCI name: Sodium Laureth Sulfate (Cognis) |
| Stabylen ® 30 | INCI name: Acrylates/Vinylisododecanoate Crosspolymer (3V Sigma) |
| Cetiol OE | INCI name: Dicapryl Ether (Cognis) |
| Turpinal ® SL | approx. 58 to 61% active substance content; INCI name: Etidronic Acid, Aqua (Solutia) |

Hydrenol D and Lorol were melted together at 80° C., then Texapon NSO, Stabylen 30, Cetiol OE, and Turpinal SL were incorporated in that order while stirring. Sodium silicate 40/42 and ammonium sulfate were each pre-dissolved in a small quantity of water and added, again while stirring. Lastly, the ammonia was added at a temperature of approx. 40° C. The weight was brought up to 100% with water while stirring, and the formulation was stirred until cold.

2.2 Mixing with the Developer Dispersion

The hair-bleaching creams produced in 2.1 were each mixed at a 1:1 ratio with a developer dispersion made up as follows:

| Raw material | Wt % |
|---|---|
| Ammonia, 25% | 0.62 |
| Dipicolinic acid | 0.10 |
| Disodium pyrophosphate | 0.03 |
| Turpinal SL | 1.50 |
| Texapon NSO | 2.00 |
| Dow Corning DB 110 A (nonionic silicone emulsion) | 0.07 |
| Aculyn 33A (acrylic polymer) | 12.00 |
| Hydrogen peroxide, 50% | 22.40 |
| Water | to 100 |

Aculyn ® 33A approx. 28% solids in water; INCI name: Acrylates Copolymer

For the hair-bleaching process, a four-fold quantity of the completed utilization mixture was applied onto strands of dark blond, light brown, and dark brown hair (codes: Kerling 7/0, Fischbach & Miller 6923, and Kerling 2/0), weighing approx. 0.7 g. After the strands had been bleached for 30 minutes at 32° C., they were washed with a commercially usual shampoo and dried with a hair dryer.

2.3 Evaluation of Lightening Performance

Each hair strand was measured colorimetrically before and after the bleaching operation. The indicator used for the lightening performance of the respective formulation was the $\Delta L$ value, in accordance with the following formula:

$$\Delta L = L_{after} - L_{before}$$

$L_{after}$=brightness of strand after bleaching
$L_{before}$=brightness of strand after bleaching.

Two determinations were made for each formulation and each hair type, and an average was calculated for each of the individual values. The higher the $\Delta L$ value, the better the lightening performance of the respective formulation.

2.4 Lightening Performance with N-[(4-Methoxyphenyl)Methylidene]Benzenesulfonamide (Activator 2)

| Hair type | $\Delta L$ (formulation C1) | $\Delta L$ (formulation I1) | $\Delta\Delta L$ |
|---|---|---|---|
| Dark blond (Kerling 7/0) | 11.0 | 11.8 | 1.0 |
| Light brown (Fischbach & Miller 6923) | 10.6 | 11.3 | 0.7 |
| Dark brown (Kerling 2/0) | 4.0 | 4.5 | 0.5 |

3. Hair-Bleaching Examples

Hair Bleaching with Hydrogen Peroxide and Persulfates 3.1 Producing a Hair Bleaching Cream Hair-bleaching creams were produced as follows using the following ingredients:

| | Wt % | |
|---|---|---|
| Raw material | C2 | I2 |
| Hydrenol D | 8.00 | 8.00 |
| Eumulgin B2 | 0.45 | 0.45 |
| Lorol C12-C18 tech. | 3.00 | 3.00 |
| Texapon NSO | 16.00 | 16.00 |
| Dehyton K | 10.00 | 10.00 |
| Monoethanolamine | 8.00 | 8.00 |
| L-Arginine | 1.00 | 1.00 |
| Turpinal SL | 0.20 | 0.20 |
| Sodium silicate 40/42 | 0.50 | 0.50 |
| N-[(4-methoxyphenyl)methylidene]benzenesulfonamide (activator 2) | — | 2.00 |
| Water | to 100 | |

Eumulgin B2  INCI name: Ceteareth-20 (Cognis)
Dehyton K  approx. 30 wt% active substance; INCI name: Cocamidopropyl Betaine (Cognis)

Firstly, Hydrenol D, Eumulgin B2, Lorol C12-C18 tech., Texapon NSO, and Dehyton K were melted together at 80° C. This melt was mixed with part of the quantity of water, and the mixture was vigorously and thoroughly mixed. The indicated quantities of the remaining constituents were then added while stirring continued, and the formulation was allowed to cool to room temperature. Formulation C2 is the comparison formulation not according to the present invention with no hair-bleaching activator; formulation I2 is the example according to the present invention having activator 2.

3.2 Mixing with the Developer Dispersion

The hair-bleaching creams were each mixed at a 1:1 ratio with a developer dispersion made up as follows:

| Raw material | Wt % |
|---|---|
| Caustic soda solution, 45% | 0.73 |
| Dipicolinic acid | 0.10 |
| Disodium pyrophosphate | 0.03 |
| Turpinal SL | 1.50 |
| Texapon NSO | 2.00 |
| Dow Corning DB 110 A (nonionic silicone emulsion) | 0.07 |
| Aculyn 33A (acrylic polymer) | 15.00 |
| Hydrogen peroxide, 50% | 22.40 |
| Water | to 100 |

3.3 Addition of Persulfate I 100 g of the mixture obtained according to 3.2 was then also mixed with 8.33 g potassium peroxodisulfate. The pH of this completed utilization mixture was from 9 to 10.2. For the hair-bleaching process, a four-fold quantity of the completed utilization mixture was applied onto strands of dark blond, light brown, and dark brown hair (codes: Kerling 7/0, Fischbach & Miller 6923, and Kerling 2/0), weighing approx. 0.7 g. After the strands had been bleached for 30 minutes at 32° C., they were washed with a commercial shampoo and dried with a hair dryer.

3.4 Addition of Persulfate II 100 g of the mixture obtained according to 3.2 was mixed with 20 g of a mixture of ammonium peroxodisulfate, sodium peroxodisulfate, and potassium peroxodisulfate. The pH of this completed utilization mixture was between 9 and 10.2. For the hair-bleaching process, a four-fold quantity of the completed utilization mixture was applied onto strands of dark blond, light brown, and dark brown hair (codes: Kerling 7/0, Fischbach & Miller 6923, and Kerling 2/0), weighing approx. 0.7 g. After the strands had been bleached for 30 minutes at 32° C., they were washed with a commercially usual shampoo and dried with a hair dryer.

3.5 Lightening Performance with N-[(4-Methoxyphenyl)Methylidene]Benzenesulfonamide (Activator 2)

| Hair type | ΔL (formulation C2 + persulfate I) | ΔL (formulation I2 + persulfate I) | ΔΔL |
|---|---|---|---|
| Dark blond (Kerling 7/0) | 18.7 | 20.5 | 1.8 |
| Light brown (Fischbach & Miller 6923) | 19.5 | 19.6 | 0.1 |
| Dark brown (Kerling 2/0) | 9.0 | 9.6 | 0.6 |

| Hair type | ΔL (formulation C2 = persulfate II) | ΔL (formulation I2 + persulfate II) | ΔΔL |
|---|---|---|---|
| Dark blond (Kerling 7/0) | 27.9 | 28.0 | 0.1 |
| Light brown (Fischbach & Miller 6923) | 25.1 | 27.8 | 2.7 |
| Dark brown (Kerling 2/0) | 16.4 | 18.1 | 1.7 |

3.6 Interpretation of the Results

An estimate as to the bleaching effects of the various formulations can be arrived at by comparing the ΔL values. It is clearly evident that higher ΔL values can be obtained by adding the hair bleaching activator. The lightening capability of the formulation was thus significantly intensified by addition of the activator. Bleaching experiments using a combination of hydrogen peroxide, peroxodisulfate salts, and the sulfonimine derivative according to the present invention also showed a better lightening performance than could be achieved when using a comparable hair-bleaching formula without the activator.

We claim:

1. Agent for lightening keratinic fibers comprising, in a cosmetic carrier:
    (i) at least one oxidizing agent chosen from hydrogen peroxide and/or a solid addition product thereof with organic or inorganic compounds, and
    (ii) at least one sulfonimine of formula (I)

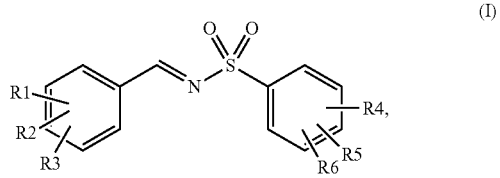

(I)

wherein
    R1 to R6 are, mutually independently, a hydrogen atom, a halogen atom, a $C_1$ to $C_6$ alkyl group, a partly or entirely halogenated $C_1$ to $C_6$ alkyl group, a $C_2$ to $C_6$ alkenyl group, a $C_1$ to $C_6$ hydroxyalkyl group, a $C_2$ to $C_6$ polyhydroxyalkyl group, a $C_1$ to $C_6$ alkoxy group, a $C_1$ to $C_6$ alkoxy-$C_2$ to $C_6$ alkyl group, an aryl-$C_1$ to $C_6$ alkyl group, a hydroxy group, a nitrile group, a nitro group, a carboxylic acid group, a sulfonic acid group, a sulfonamido group, an amino group, a di-$C_1$ to $C_6$ alkylamino group, a mono-$C_1$ to $C_6$ alkylamino group, a $C_1$ to $C_6$ alkoxycarbonyl group, an optionally substituted aryl group, or an optionally substituted heteroaryl group,
    wherein two residues chosen from R1, R2, and R3 and/or two residues chosen from R4, R5, and R6 can each form with one another and with the adjacent benzene ring a fused aromatic or heteroaromatic five- or six-membered cycle.

2. Agent according to claim 1 wherein the at least one sulfonimine according to formula (I) is at least a compound wherein at least one of the residues R1, R2, and R3 and/or R4, R5, R6 is a hydrogen atom.

3. Agent according to claim 1 wherein the at least one sulfonimine according to formula (I) is at least a compound wherein at least one of the residues R1, R2, and R3 and/or R4, R5, R6 is a hydroxy group, a $C_1$ to $C_6$ alkoxy group, a halogen atom, a nitro group, or a carboxylic acid group.

4. Agent according to claim 1 wherein the at least one sulfonimine according to formula (I) is at least a compound chosen from N-(phenylmethylidene)benzenesulfonamide, N-[(4-chloro-phenyl)methylidene]benzenesulfonamide, 4-chloro-N-(phenylmethylidene)benzenesulfonamide, 4-{[(phenylsulfonyl)imino]methylidene}benzoic acid, 4-{[(phenylmethylidene)amino]sulfonyl}benzoic acid, N-[(4-methylphenyl)methylidene]benzenesulfonamide, 4-methyl-N-(phenylmethylidene)benzenesulfonamide, N-[(4-hydroxyphenyl)methylidene]benzenesulfonamide, 4-hydroxy-N-[(phenylmethylidene)benzenesulfonamide, N-[(4-methoxyphenyl)methylidene]benzenesulfonamide, 4-methoxy-N-(phenylmethylidene)benzenesulfonamide, N-[(4-nitro-phenyl)methylidene]benzenesulfonamide, 4-nitro-N-(phenylmethylidene)benzenesulfonamide, 4-({[(4-chlorophenyl)methylidene]amino}sulfonyl)benzoic acid, 4-({[(4-chlorophenyl)sulfonyl]imino}methyl)benzoic acid, N-[(4-hydroxy-3-methoxyphenyl)methylidene]benzenesulfonamide, 4-chloro-[(4-hydroxy-3-methoxyphenyl)methylidene]benzenesulfonamide, 4-({[(4-hydroxy-3-methoxyphenyl)methylidene]amino}sulfonyl)benzoic acid, N-[(4-hydroxy-2-methoxyphenyl)methylidene]benzenesulfonamide, 4-chloro-[(4-hydroxy-2-methoxyphenyl)methylidene]benzenesulfonamide, 4-({[(4-hydroxy-2-methoxyphenyl)methylidene]amino}sulfonyl) benzoic acid, and 4-chloro-N-[(4-methoxyphenyl) methylidene]benzenesulfonamide.

5. Agent according to claim 1 wherein the at least one sulfonimine according to formula (I) is at least N-[(4-methoxyphenyl)methylidene]benzenesulfonamide.

6. Agent according to claim 1 wherein the at least one sulfonimine according to formula (I) is present in an amount of from 0.01 to 25 wt %, based on total weight of the ready-to-use agent.

7. Agent according to claim 1 wherein the at least one oxidizing agent is at least an aqueous solution of hydrogen peroxide.

8. Agent according to claim 1 further comprising at least one inorganic persulfate salt or peroxodisulfate salt.

9. Agent according to claim 8 wherein the at least one inorganic persulfate salt or peroxodisulfate salt is chosen from ammonium peroxodisulfate, potassium peroxodisulfate, sodium peroxodisulfate, and mixtures thereof.

10. Agent according to claim 1 further comprising at least one alkalizing agent chosen from ammonia, alkanolamines and basic amino acids.

11. Method for lightening keratinic fibers comprising:
    applying an agent according to claim 1 onto the keratin-containing fibers,
    leaving the agent on the fibers for 5 to 60 minutes, and
    rinsing out with water or washing out with a shampoo the agent from the keratin-containing fibers.

12. Multi-component packaging unit for lightening keratinic fibers comprising, in containers packaged separately from one another:

at least one oxidizing-agent preparation (B) containing hydrogen peroxide or a solid addition compound of hydrogen peroxide with inorganic or organic compounds, and at least one preparation (A) comprising, in a cosmetic carrier, at least one sulfonimine of formula (I)

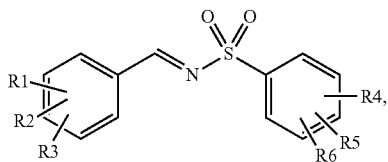

wherein

R1 to R6 are, mutually independently, a hydrogen atom, a halogen atom, a $C_1$ to $C_6$ alkyl group, a partly or entirely halogenated $C_1$ to $C_6$ alkyl group, a $C_2$ to $C_6$ alkenyl group, a $C_1$ to $C_6$ hydroxyalkyl group, a $C_2$ to $C_6$ polyhydroxyalkyl group, a $C_1$ to $C_6$ alkoxy group, a $C_1$ to $C_6$ alkoxy-$C_2$ to $C_6$ alkyl group, an aryl-$C_1$ to $C_6$ alkyl group, a hydroxy group, a nitrile group, a nitro group, a carboxylic acid group, a sulfonic acid group, a sulfonamido group, an amino group, a di-$C_1$ to $C_6$ alkylamino group, a mono-$C_1$ to $C_6$ alkylamino group, a $C_1$ to $C_6$ alkoxycarbonyl group, an optionally substituted aryl group, or an optionally substituted heteroaryl group, wherein two residues chosen from R1, R2, and R3 and/or two residues chosen from R4, R5, and R6 can each form with one another and with the adjacent benzene ring a fused aromatic or heteroaromatic five- or six-membered cycle.

13. Multi-component packaging unit according to claim 12 further comprising, in a separately packaged container, at least one hair-bleaching powder (C) comprising at least one inorganic peroxodisulfate salt chosen from ammonium peroxodisulfate, potassium peroxodisulfate, and/or sodium peroxodisulfate.

* * * * *